US008652039B2

(12) United States Patent
Rosales et al.

(10) Patent No.: US 8,652,039 B2
(45) Date of Patent: Feb. 18, 2014

(54) GUIDING DIFFERENTIAL DIAGNOSIS THROUGH INFORMATION MAXIMIZATION

(75) Inventors: Romer E. Rosales, Downingtown, PA (US); Marianne Larissa Mueller, West Chester, PA (US); Sriram Krishnan, Exton, PA (US); R. Bharat Rao, Berwyn, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1512 days.

(21) Appl. No.: 11/365,271

(22) Filed: Mar. 1, 2006

(65) Prior Publication Data
US 2006/0200010 A1    Sep. 7, 2006

Related U.S. Application Data

(60) Provisional application No. 60/657,855, filed on Mar. 2, 2005.

(51) Int. Cl.
*A61B 5/00* (2006.01)
*G06F 19/00* (2011.01)

(52) U.S. Cl.
CPC ..................... *G06F 19/34* (2013.01)
USPC .............................. 600/301; 705/2

(58) Field of Classification Search
USPC .................. 600/300–301; 705/2–4
See application file for complete search history.

(56) References Cited

U.S. PATENT DOCUMENTS

| | | | |
|---|---|---|---|
| 4,731,725 A * | 3/1988 | Suto et al. ..................... 706/46 |
| 5,839,438 A | 11/1998 | Graettinger et al. .......... 128/630 |
| 6,283,761 B1 | 9/2001 | Joao | |
| 6,398,728 B1 * | 6/2002 | Bardy ......................... 600/300 |
| 6,770,029 B2 * | 8/2004 | Iliff ............................ 600/300 |
| 7,729,762 B2 * | 6/2010 | Sun et al. ....................... 607/5 |
| 2002/0029157 A1 | 3/2002 | Marchosky | |
| 2003/0101076 A1 * | 5/2003 | Zaleski ........................... 705/2 |
| 2004/0260666 A1 * | 12/2004 | Pestotnik et al. ............... 706/46 |
| 2005/0065813 A1 * | 3/2005 | Mishelevich et al. ............ 705/2 |
| 2005/0222868 A1 * | 10/2005 | Kantrowitz ..................... 705/2 |
| 2009/0125322 A9 * | 5/2009 | Dahlin et al. .................... 705/2 |

FOREIGN PATENT DOCUMENTS

| | | |
|---|---|---|
| EP | 0 531 889 A | 3/1993 |
| WO | WO 98/02836 A | 1/1998 |
| WO | WO 01/71634 A1 | 9/2001 |
| WO | WO 02/33654 A1 | 4/2002 |
| WO | WO 03/032827 A | 4/2003 |

OTHER PUBLICATIONS

C. Shannon, "A Mathematical Theory of Communication" Bell System Technical Journal 27 (1948), 379-423, 623-656.
International Search Report including Notification of Transmittal of the International Search Report, International Search Report and Written Opinion of the International Searching Authority, PCT Appln No. PCT/US2006/007222, mailed Sep. 6, 2006.

* cited by examiner

*Primary Examiner* — Bill Thomson
*Assistant Examiner* — Bobby Soriano
(74) *Attorney, Agent, or Firm* — Joshua B Ryan (57) ABSTRACT

A system and method for diagnosis and treatment decisions based on information maximization is disclosed. Utilizing patient information as well as clinical records from other patients can reduce the uncertainty in both diagnosis and treatment options. The information maximization may consider additional data such as risk, cost, and comfort in making a proper medical decision.

18 Claims, 4 Drawing Sheets

GUIDING DIFFERENTIAL DIAGNOSIS THROUGH INFORMATION MAXIMIZATION

RELATED APPLICATIONS

The present patent document claims the benefit of the filing date under 35 U.S.C. §119(e) of Provisional Patent Application No. 60/657,855, filed on Mar. 2, 2005, which is hereby incorporated by reference.

BACKGROUND

The present disclosure relates to differential diagnosis through information maximization and benefit maximization.

During patient care, health care workers are faced with the problem of arriving at a diagnosis decision or action plan for diagnosis at multiple time instances, such as after observing patient's symptoms or after gathering new clinical findings from laboratory tests or other sources. These decisions are critical when making a diagnosis or determining a proper treatment for a patient. However, in most cases, there is no unique and clear diagnosis or obvious action plan. Even after a patient's medical history has been gathered and some tests performed, there can still be considerable uncertainty in many cases regarding the correct diagnosis or method of treatment. At all points in the diagnosis or decision process, the clinician is faced with numerous questions or options regarding what may be the best course of action. The clinician determines whether sufficient information has been collected so that a reliable diagnosis or decision can be rendered. In addition, the clinician must properly arrive at the correct diagnosis or decision while considering the most efficient use of resources.

The difficulty for decision-making applies to a diagnosis of an illness or disease, as well as any decision regarding further treatment or therapy for that illness or disease. Regardless of whether the clinician decision is for diagnosis or treatment, a decision is made based on a wide-range of considerations and based on a broad array of data that is available to assist in the decision. For example, the clinician faces many challenges while making a decision about therapy, such as which therapy to choose, when should therapy be chosen, or whether more information should be collected.

Specifically considering diagnosis, the clinician may use differential diagnosis. Differential diagnosis is a systematic method for diagnosing a disorder that lacks unique symptoms or signs, such as a headache. In differential diagnosis, the clinician considers possible causes before making a diagnostic decision. Often, the clinician must consider multiple causes of the observed findings. This is a process that can quickly grow in complexity if carried out thoroughly and comprehensibly.

It is not uncommon to find cases where there are many potential causes that could all explain a patient's condition. Likewise, there may be many available testing procedures given the specific patient's condition that have relatively unclear advantages over each other. The process can be complicated when medical research has not yet given clear cut results regarding the connection between the specific patient symptoms, tests, and diseases.

The decision about what causes (e.g., disorders) to consider may be influenced by the clinician's experience, judgment, preferences, and/or limited available information. These factors can be highly variable among medical practitioners. A more uniform, informed, and objective form of differential diagnosis may be highly beneficial for health care.

BRIEF SUMMARY

By way of introduction, the preferred embodiments described below include methods and instructions in computer readable media for making a medical diagnosis or selecting the appropriate treatment or therapy for a medical condition. In one embodiment, a new method for computer-aided differential diagnosis is disclosed that is based on formal information theoretic and probabilistic modeling concepts. The method makes use of available data, such as previously recorded cases, to provide a probabilistic approach for differential diagnosis. Differential diagnosis may include both the diagnosis of an illness, disease, or medical condition, or may relate to the treatment, therapy, or tests used in response to a medical condition.

In a first aspect, a method is provided for developing at least one medical decision. The method includes: obtaining patient medical data; obtaining other medical data from existing clinical records; analyzing the patient medical data and the other medical data with a processor; identifying the at least one medical decision based on the analysis of the patient medical data and the other medical data; and determining a probability for each of the at least one medical decision based on the analysis of the patient medical data and the other medical data.

In a second aspect, a computer readable storage medium includes instructions executable by a programmed processor for determining at least one medical approach. The instructions include: providing patient observations including patient medical data; providing clinical observations based on recorded clinical data; comparing the patient observations with the clinical observations; selecting relevant observation data from the clinical observations, wherein the relevant observation data is relevant for analyzing the at least one medical approach; and determining the at least one medical approach based on the relevant observation data.

In a third aspect, a method is provided for determining a test for a medical condition. The method includes: choosing the medical condition to be treated; providing patient observations; providing existing clinical data; analyzing with a processor the existing clinical data to find observations based on at least one chosen test to determine the effectiveness of the at least one chosen test; and determining the effectiveness of each of the at least one chosen test.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention.

DETAILED DESCRIPTION OF THE DRAWINGS AND THE PRESENTLY PREFERRED EMBODIMENTS

An important consideration for clinician's to consider when analyzing the difficulties faced by health care decision-making is that large amounts of recorded clinical data may potentially be available to aid in analysis. This clinical data includes recorded patient visits, diagnosis, laboratory tests, treatments, therapy results, images, and/or other information. In current medical practice, this large amount of recorded information is of little or no immediate (real-time) use in the diagnosis of a new and seemingly unrelated patient. A major reason for ignoring this information is that analysis of this data requires expert knowledge and considerable time and effort to decipher the data. In order to make efficient use of the wealth of recorded clinical data, the most relevant data is filtered out from the data that is not relevant to a given patient's situation.

A computer system that could appropriately handle the large amounts of information and processing loads to filter through existing clinical and current patient records may help. However, more important than processing power is the need for a sound method to properly assist in such a scenario. The proper use of available information from previous patient records may significantly aid the clinician in making patient specific decisions in order to efficiently achieve a proper diagnosis or decision on treatment.

The proposed embodiments present a method for computer-aided differential diagnosis based on formal information theoretic and probabilistic modeling concepts. The embodiments make use of the available data (such as previously recorded cases) to provide a probabilistic and sound approach for differential diagnosis. The embodiments may provide a program that can be used in real-time in a hospital, health care facility, or any medical related institution. A clinician can input data and receive results at the hospital in real-time to assist in making diagnoses and choosing treatment, tests or therapy.

The following description considers both the scenarios of diagnosis of a medical condition and treatment/therapy decisions for the medical condition. It should be understood, however, that both scenarios may be combined and may collectively be referred to as medical choices, decisions, observations or selections. Differential diagnosis may refer to diagnosing a medical condition or selecting a treatment or therapy. In at least one embodiment, the system proposed below may be used to both diagnose and select treatment/therapy for the diagnosed medical condition. For simplicity, one or both of diagnosis and treatment may be referred to below.

The proposed embodiments may include finding a single best decision given current information, proposing efficient decision paths or courses of action, or proposing different paths under various types of constraints. Also considered is the incorporation of features such as risk to the patient, cost, effectiveness, patient discomfort, or other considerations. In addition, when finding a decision, a factor whether enough information and certainty are present to make a proper diagnosis may be considered. In case the answer to this is negative, the next best course of action is considered, such as what should be measured or tested next.

Figure 1:
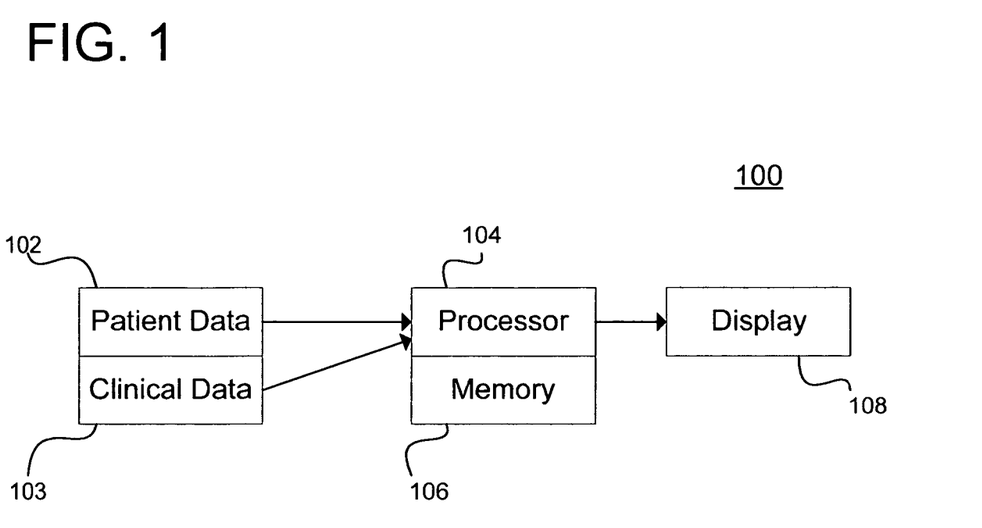
FIG. 1 is a block diagram of one embodiment of a system for information maximization or maximization of another criteria such as benefit maximization.

FIG. 1 is a block diagram of one embodiment of a system 100 for information maximization. The system 100 includes a processor 104, a memory 106 and a display 108. The input into the processor 104 may be either patient data 102 or clinical data 103, or both. Additional, different or fewer components may be provided. The system 100 may include a personal computer, workstation, medical diagnostic imaging system, network, or other now known or later developed system for analyzing and classifying medical information to develop a diagnosis or decision with a processor. The system 100 is a computer aided system for either diagnosis or treatment/therapy recommendations. Automated assistance may be provided through an output or the display 108 to a physician for diagnosing a medical condition, or choosing treatment for that medical condition. In one embodiment, assistance may be provided for diagnosis or treatment of breast cancer utilizing records from past breast cancer tests.

The patient data 102 is medical data from one or more sources of patient information. The patient data 102 may also be referred to as patient information, patient observations, or patient records. Patient data 102 may be medical data collected over the course of a patient's treatment, or patient history, recorded patient visits, family history, demographic information, symptoms, disease, illness, or other indicators of likelihood related to the medical condition detection being performed. The demographic information may include age, sex, physical activity, dietary records, or any factors related to a patient's health. For example, whether a patient smokes, is diabetic, is male, has a history of cardiac problems, has high cholesterol, has a high systolic blood pressure or is old may indicate increase the likelihood of a given medical condition and be considered as patient data 102.

Patient data 102 may include results from any tests, treatments, therapy or medical process. For example, medical imaging could be tests that comprise part of the patient data 102. Examples of medical imaging tests may include ultrasound, magnetic resonance imaging ("MRI"), nuclear medicine, mammography, positron emission tomography ("PET") scan, x-ray, computer thermography, angiography, and/or other now known or later developed imaging modality, which all may be patient data 102.

Patient data 102 may be based on observations from the patient or observations from a clinician about that patient. In one embodiment, the patient data 102 is stored in memory 108. The clinician may also be able to input the patient data 102 into the system 100 including any new data, such as any new symptoms the patient may have and any changes to the existing patient data 102. Alternatively, patient data 102 may be determined by processor 104 from system 100 and according to the methods proposed below. Specifically, if a diagnosis is made, then that diagnosis information will be added in as part of the patient data 102.

The clinical data 103 may be any existing medical records. The clinical data may also be referred to as clinical records, other/existing medical data, other/existing clinical records, other/existing clinical data, clinical observations, other/existing clinical observations, or recorded clinical observations. Clinical data 103 may be a collection of patient data from a large subset of patients collected over time. The existing patient data used for the clinical data 103 may include the same or different factors as the patient data 102, described above. Specifically, the clinical data 103 may include medical data collected over the course of a patient's treatment/therapy, patient history, recorded patient visits, family history, demographic information, symptoms, or other indicators of likelihood related to the medical condition detection being performed or any factors related to a patient's health. Additionally, recommendations or other procedures provided by a medical institution, association, society or other group may be included with the clinical data 103, such as providing domain knowledge.

There may be a vast or limited amount of clinical data 103 available based on a very large or small number of patients. For example, the clinical data 103 represents a study of many past patients. As another example, the clinical data 103 includes representative samples of different information. The system 100 analyzes the clinical data 103 with the information that is known about the current patient (patient data 102) to make informed choices or selections regarding diagnosis or treatment decisions.

The processor 104 may be one or more general processors, digital signal processors, application specific integrated circuits, field programmable gate arrays, servers, networks, digital circuits, analog circuits, combinations thereof, or other now known or later developed devices for analyzing patient and clinical data. The processor 104 may implement a software program, such as code generated manually (i.e., programmed) for a diagnostic system. The processor 104 may implement a probability model or graphical model (e.g., Bayesian network, factor graphs, chain graph, or hidden or random Markov models), a boosting based model, a decision tree, a neural network, combinations thereof or other now known or later developed algorithm. The diagnostic software is configured or trained for receiving and analyzing patient and clinical data and identifying options and associated probabilities for those options.

In one embodiment, the processor 104 implements a model or diagnostic system programmed with potential diagnoses or treatments and the system determines which are the most appropriate based on the given data. In response to patient data 102 determined by a processor or input by a user, the system analyzes existing clinical data 103. In an alternative embodiment, the system 100 is implemented using machine learning techniques, such as training a neural network using sets of training data obtained from a database of patient cases with known diagnosis. The system 100 analyzes patient data 102 with the clinical data 103 and outputs a diagnosis. The learning may be an ongoing process or be used to program a filter or other structure implemented by the processor 104 for later existing cases.

The memory 106 is a computer readable storage media. Computer readable storage media may include various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one embodiment, the instructions are stored on a removable media drive for reading by a medical diagnostic system or a workstation networked with similar systems. A diagnostic system or work station uploads the instructions. In another embodiment, the instructions are stored in a remote location for transfer through a computer network or over telephone lines to the diagnostic system or workstation. In yet other embodiments, the instructions are stored within the diagnostic system on a hard drive, random access memory, cache memory, buffer, removable media or other device.

The memory 106 is operable to store instructions executable by the processor 104. The instructions are for analyzing patient data 102 and clinical data 103 to make a diagnosis or treatment decisions. The functions, acts or tasks illustrated in the figures or described herein are performed by the programmed processor 104 executing the instructions stored in the memory 106. The functions, acts or tasks are independent of the particular type of instructions set, storage media, processor or processing strategy and may be performed by software, hardware, integrated circuits, film-ware, micro-code and the like, operating alone or in combination. Likewise, processing strategies may include multiprocessing, multitasking, parallel processing and the like.

Patient data 102 and clinical data 103 are input to the processor 104 or the memory 106. The input may be made through an interface (not shown) such as a keyboard or a mouse coupled with the processor or with the display 108. The input may also be obtained through data transmitted via the network or internet, from storage media (such as a hard drive), from a medical device or other device coupled to the processor that can provide the relevant data. The patient data 102 or the clinical data 103 may be stored in memory 106. The user may edit or add to either the patient data 102 or the clinical data 103 through an interface with either the processor 104, the memory 106 or the display 108. Alternatively or additionally, the input is through data transfer or processor driven collection (mining) of information.

The instructions in the memory 106 cause the processor 104 to output diagnosis or treatment results. The results may be displayed as numbers, text, a graph or an image on the display 108. The results may also be stored in the memory 106. The display 108 may be a CRT, monitor, flat panel, LCD, projector, printer or other now known or later developed display device for outputting determined information. For example, the processor 104 causes the display 108 at a local or remote location to output data indicating a selection associated with a given medical condition, probability associated with the one or more selections, or other process related information. The output may be stored with or separate from the patient and clinical medical data.

Figure 2:
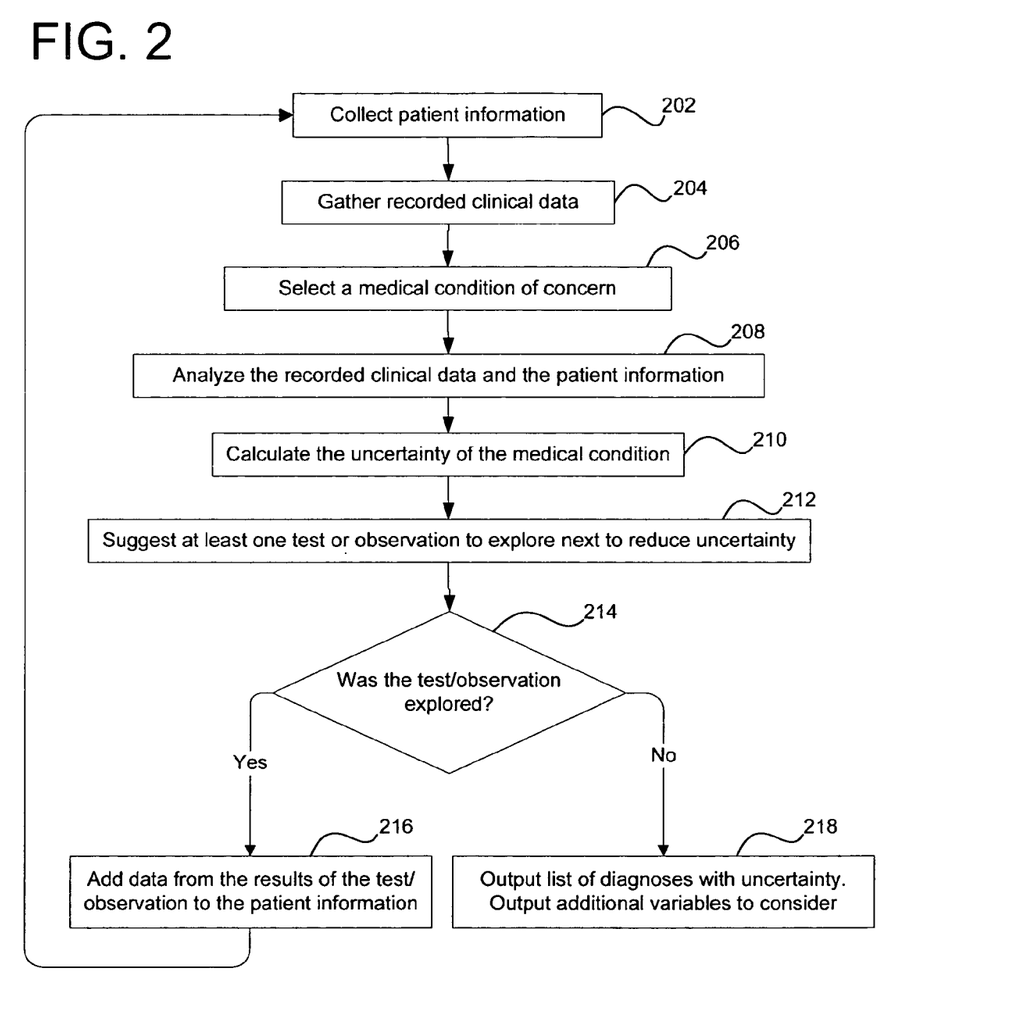
FIG. 2 is a flowchart diagram of one embodiment of differential diagnosis.

FIG. 2 is a flowchart diagram of one embodiment of differential diagnosis. This embodiment is implemented by the system 100 of FIG. 1 or a different system. Additional, different or fewer acts may be used.

In act 202, patient information is collected for a specific patient. As discussed above with regard to FIG. 1, patient data 102 can be a variety of information related to the patient's medical history. The patient information may be stored in memory 106, or may be input into the processor 104 according to FIG. 1. In one embodiment, a clinician can add patient information to the existing patient data that is already stored in the system.

Likewise, in Act 204, recorded clinical data is gathered. As discussed above with regard to FIG. 1, recorded clinical data 103 includes patient data from a set of past patients. In one embodiment, the recorded clinical data 103 is a large database of any relevant medical data that may be useful for diagnosis or treatment of a medical condition and may be stored in memory 106. As with patient information, recorded clinical data may be added to by a clinician or health care worker. In one embodiment, the database is continually growing as more health care facilities add records and data to the database. In an alternate embodiment, the recorded clinical data that is gathered may be a subset of a larger group of clinical data. For example, to determine a diagnosis or treatment for breast cancer, the recorded clinical data may be a database of a specially designed breast cancer study. In the study, each of the patients may have undergone all the most relevant tests, which were analyzed to diagnose cancer.

In act 206, a medical condition of concern is chosen to be analyzed based on the patient information and the recorded clinical data. The medical condition of concern may also include a disease of concern, an outcome of a particular therapy of concern, or other variable of interest. For example, the clinician may be interested in whether a patient has breast cancer, then breast cancer would be the medical condition of concern. A clinician or physician may make an initial diagnosis of a condition and that condition would then be used with system 100 for an analysis of all the patient and clinical data. In an alternate embodiment, the system 100 would compare the patient information with the clinical data and make a determination as to a probable diagnosis.

In act 208, the patient information and recorded clinical data is analyzed to determine whether the medical condition of concern is present in the patient. The analysis may be a comparison of the patient data with similar clinical records that would indicate possible diagnoses and treatments appropriate for the patient. The analysis may use clinical records that are considered to be probabilistically relevant for the variable of interest and the function to be maximized. One example of this analysis is discussed in the embodiment for FIG. 3 on information maximization.

In act 210, the uncertainty or probability is determined regarding the medical condition. This step may include calculating the conditional probability of the medical condition of interest given the information that has been gathered. It may also include the same conditional distribution also conditioned on observing at least one of the available medical tests or potential next steps to consider by a clinician. As in act 208, a comparison of patient information and the recorded clinical data may be used to determine the likelihood of the existence of the medical condition. The comparison may consider the clinical data that is most similar to the patient data and determine which diagnosis and treatment was used for those patients. For example, if the patient suffers from unique symptoms, then an analysis of the clinical data of patients with those symptoms, but also comparing all the other relevant patient information, such as demographics, can produce a probability regarding a diagnosis or possible treatment.

The determination of relevant patient information may be based on a number of factors. The relevant data may merely be those records that contain similar information to the current patient information. Conversely, even though clinical data does not appear similar to the patient data, this nonetheless may be relevant since the probabilistic model may capture indirect relationships between the variables. If breast cancer is the medical condition of concern, then the analysis in act 208 and the uncertainty in act 210 are a measure whether the patient has breast cancer. A further example of the uncertainty calculation is described with FIG. 3.

Once an analysis is made as to the medical condition of concern, further tests or observations may be considered which may improve the analysis or increase the certainty regarding the presence of the medical condition as in act 212. For example, if the medical condition is breast cancer, there may be a variety of tests available, which may assist in determining whether breast cancer is present in a patient. For example, the tests that may be available could be mammography, ultrasound, PET scan, an MRI, or another relevant test. Act 212 may result in at least one of those tests being suggested as providing increased certainty for a diagnosis of breast cancer. A value indicating the current uncertainty before any new tests and the reduction in uncertainty that can be achieved in the best/worst/average case if selecting each test may be displayed along with at least one of the possible tests. The test recommended by the system can be indicated explicitly. As in acts 208 and 210, the suggestion may be based on a comparison of the patient information with the clinical data to make a determination which tests were most effective based on the clinical records.

After a test or observation is suggested according to act 212, whether the test is performed or the observation is made is determined in act 214. A user can determine whether to perform the observation (e.g., perform the test on the patient) based on multiple factors including: target uncertainty, target risk, cost, etc. The output may include the probability or certainty of the presence of the medical condition of concern along with any other possible diagnoses and associated probabilities. Also, a list of additional tests or observations may be provided that may assist in diagnosis. If the test was performed, then the results of the test become part of the patient information as in act 216. The process can then be repeated beginning with act 202, which includes an updated version of patient information that includes the test results. This second iteration should now result in improved certainty regarding the presence of the medical condition of concern or another more appropriate diagnosis. For example, if an MRI is suggested according to act 212 and the MRI is performed, then the test results become a part of the patient information and is further data used to determine if a patient has breast cancer. That additional information can then be used to compare with the clinical records on MRI's and the diagnoses that the test results may suggest.

Figure 3:
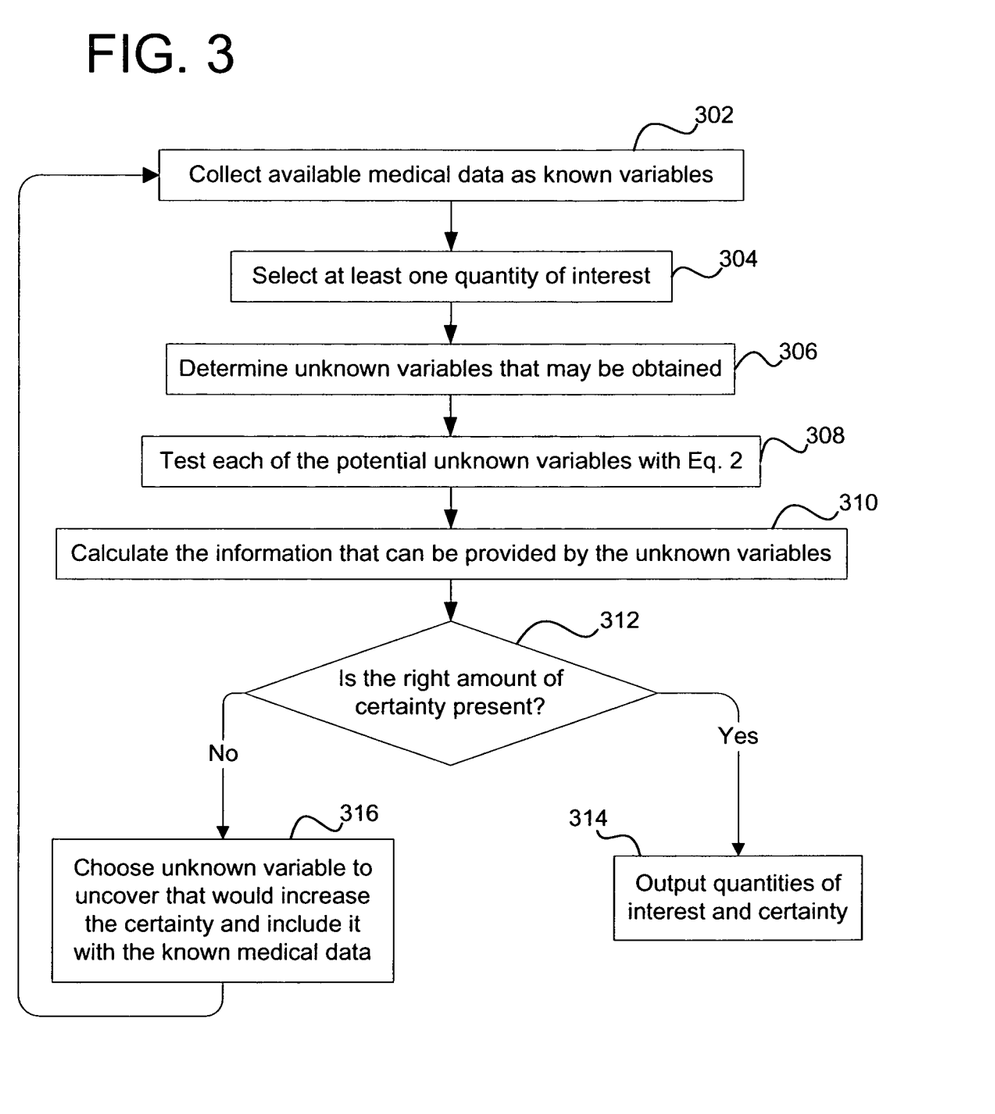
FIG. 3 is a flowchart diagram of an alternate embodiment of differential diagnosis through information maximization.

FIG. 3 is a flowchart diagram of another embodiment of differential diagnosis through information maximization. FIG. 3 represents an embodiment of information maximization utilizing formal information theoretic concepts. The embodiments described in FIG. 2 may be considered as a general method for utilizing system 100 from FIG. 1. Likewise, FIG. 3 may be a method related to that in FIG. 2, however, FIG. 3 includes embodiments of the specific equations, formulas and techniques that may be used to implement the system 100. Those equations may be part of the software program that analyzes the data to make the determinations regarding a medical decision.

In act 302, medical data is collected both from a patient and from recorded clinical data. As discussed above, the recorded clinical data may be an existing database of patient records. Each element of patient data is defined as a random variable and may be assigned to possible categories, such as demographics, symptoms, test result, or disease. Elements may be extracted from images, such as using automated or processor based image processing. The variables that are known may be denoted as Z. For example, known variables may include demographic information and patient symptoms. Also, expert knowledge or opinion may also be considered as part of the medical data. A clinician's knowledge about a variable may be considered. For example, a symptom may be excluded or test results may be modified if the clinician determines that the data is not entirely accurate or correct. The clinician has the option of editing the medical data based on expert opinion.

In act 304, a quantity of interest is determined. It is a variable in which a clinician may be ultimately interested in, but that has not been directly observed, such as the occurrence of cancer in the patient. The variable of interest is denoted as X. This variable may not be observable directly or it may be observed at a high cost. Thus, it is preferable to rely on other sources of information, such as clinical records, to try to infer the value of this variable. The variable of interest can be considered a question that needs to be answered. An example would be whether a patient has cancer or whether a particular treatment methodology should be used.

In act 306, a determination is made based on variables that may be obtained, but have not yet been obtained. Variables that have not been observed yet may be denoted as Y. An example of a variable that is not known may be the result of a lab test. The collection, selection or determination of the variables X, Y, and Z may be performed by a clinician, health care worker, or patient or mined with a processor. In addition, variable X may include previously recorded clinical data from other patients.

The maximization of information is used to optimize the following equation based on variables X, Y, and Z:

$$\arg\max_{j} I(X; Y_j | Z_1 = z_1, \ldots, Z_k = z_k) \quad \text{(Eq. 1)}$$

Equation 1 is an optimization of I, which is the mutual information between the variable of interest X and the variables whose value we could potentially obtain $Y_j$, conditioned on the fact that we already know variables $Z_1=z_1, \ldots, Z_k=z_k$. The mutual information I may be considered as the degree of dependence between X and Y. Equation 1 considers which $Y_j$ maximizes the function. $Y_j$ is a representation of the unknown variables that may be obtained according to act 306, and Equation 1 represents an optimization of each of the unknown variables according to act 308. In act 308, each of the potential unknown variables may be tested according to Equation 2 as discussed below. Equation 1 and the subsequent equations are an embodiment of the analysis that is performed in act 208 of FIG. 2.

For example, consider the case of patient whom the clinician suspects may have breast cancer. X is breast cancer and Z is the known medical data including patient data and recorded clinical data. Z includes the patient's demographics, symptoms, and medical history, as well as recorded clinical data. The recorded clinical data may include records from patients who had breast cancer and their symptoms, demographics, medical history and test results. $Y_j$ are the variables that are unknown, such as any number of imaging tests that may be performed on the patient. Equation 1 utilizes each of the options for Y to determine which Y maximizes the dependence between X and Y. For example if Y is an MRI, then the mutual information I may be maximized because the recorded clinical data X of past MRI exams resulted in an accurate diagnosis. Likewise, if Y is ultrasound, then maybe the mutual information I is not as high as for an MRI because the recorded clinical data X of past ultrasound exams did not lead to definitive information.

Equation 1 is based on the joint distribution of the variables in question. Using the shorthand $z=(z_1, \ldots, z_k)$ to denote the assignment of multiple variables, this maximization problem can be rewritten as:

$$\arg\max_{j} \sum_{x} \sum_{y_j} P(x, y_j|z) \log \frac{P(x, y_j|z)}{P(x|z)P(y_j|z)} \quad \text{(Eq. 2)}$$

The set of unknown variables $Y_j$ are finite. Assuming the variables follow a multinomial joint probability distribution that can be reliably estimated, this problem can be solved by testing each of the potential candidate variables individually. In order to arrive at a diagnosis with high certainty, usually one observation is not enough. Multiple variables may be observed simultaneously. The process can be repeated iteratively until some precision or confidence level is achieved. This precision or confidence level may be set by a clinician. For example, this limit can be defined in terms of amount of information that is left in the variable of interest, also referred to as entropy.

Equation 2 results in an output of a variety of diagnoses with a probability or certainty associated with each one as in act 310, such as the amount of information that each variable $Y_j$ can provide. In act 310, a calculation may be performed regarding the information that can be provided by the unknown variables. In act 312, if the certainty is determined to be adequate, then the output may include the list of the variable(s) of interest with the certainty or probability for each one according to act 314. For example, the diagnosis of breast cancer may have 25% certainty and the diagnosis of influenza may have 50% certainty. Alternatively, considering the unknown variable Y, the probabilities may be associated with tests. For example, the results of an MRI may give a 75% probability of diagnosing breast cancer, while an ultrasound exam may only give a 40% probability of being able to diagnose breast cancer for this particular patient.

This embodiment proposes an iterative method for finding the certainties of diagnoses or treatments; however, it should also be recognized that medical expert knowledge may be used to reduce the number of iterations. For example, a clinician may have knowledge of the conditional independence relationships between treatments and diagnoses that can help make the right diagnosis or choose the right treatment. That information may be incorporated into the system. A single pass may be used in some embodiments.

In one embodiment the results may be displayed on a display 108 as in system 100 from FIG. 1. The results may list the possible variables for Y, which are tests or observations that can be made to improve diagnosis. The list may include the amount of certainty the results of the tests or observations may provide. The display 108 may also include the potential diagnoses, as well as the certainty or probability that the diagnosis applies to the patient. In one embodiment, each diagnosis may have tests or observations associated with it that could improve certainty. That certainty may be quantified as well. For example, breast cancer may be a diagnosis with a 50% probability and an MRI may be listed as a test for breast cancer that can improve the probability of the diagnosis by 25%. The display may be interactive as discussed for system 100, allowing the user to enter in additional data, such as test results that may improve the certainty.

Once a previously unknown variable has been tested and observed, it can be incorporated as part of the background knowledge according to act 316. Specifically, assuming that previously unknown $Y_o$ was observed, the following equation can now be solved:

$$\arg\max_{j \neq 0} I(X; Y_j | Z_1 = z_1, \ldots, Z_k = z_k, Y_o = y_o) \quad \text{(Eq. 3)}$$

Equation 3 is an update of the original maximization problem (Equation 1) based on the fact that $Y_o$ is now known. $Y_o$ may represent the results of a test or a new observation that can now be included in the original maximization problem. For example, $Y_o$ may be an MRI which was performed. The results of the MRI now become a known variable z, which is used for a second iteration of solving Equation 3.

Figure 4:
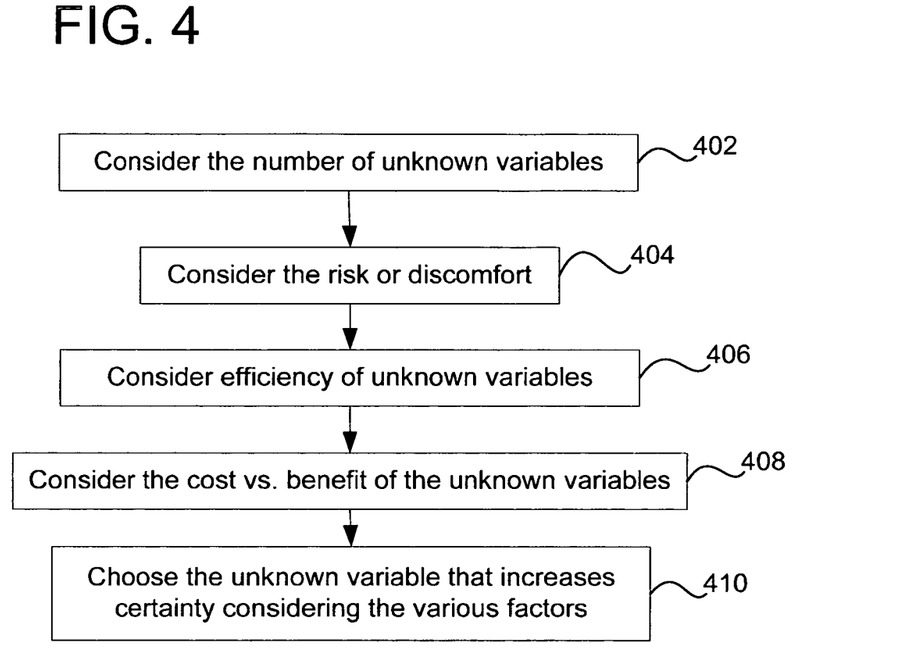
FIG. 4 is a flowchart diagram of an embodiment for choosing an unknown variable based on additional considerations.

FIG. 4 is a flowchart diagram of an embodiment for choosing an unknown variable based on additional considerations. FIG. 4 includes additional factors or considerations that may be made during the information maximization process or in general, any benefit maximization process.

Since clinical resources may be limited, it should not be assumed that the iterative process can be repeated an unlimited number of times. The problem in Equation 1 can be slightly reformulated so that the information is maximized with a further constraint on the number of variables that can be observed or equivalently the number of tests that may be performed as in act 402. In addition, constraints can be imposed on test attributes or characteristics, such as risk to the patient, cost of test, or patient discomfort, according to act 404. For example, a clinician may require that certain tests not be performed for a particular type of patient due to high health risk. These extensions require modifying the optimization problem of Equation 1 to a constrained optimization problem; however, the general idea remains the same. In particular, maybe the test cannot be performed because the patient cannot be subject to the test. In this case, the variable associated with the test is not considered a candidate to maximize Equation 2 or any substitute for Equation 2.

In some cases, the cost of observing one random variable, such as performing a test, may be negligible once another test has been performed. One example would be multiple blood tests, since once blood test A is conducted, it is easy to perform blood test B. Thus, an additional element can be added to Equation 1, so that efficiency is considered according to act 406. In this case, correlated test costs may be taken into account.

In an alternate embodiment, multiple variables may be discovered at once. This equation may be used for discovering the best combination of L variables:

$$\operatorname*{argmax}_{t} \sum_{x} \sum_{y_t} P(x, y_t|z) \log \frac{P(x, y_t|z)}{P(x|z)P(y_t|z)} \qquad \text{(Eq. 4)}$$

In Equation 4, $|t|=L$. Therefore, t indexes all the sets of L different variables. The inner summation is over the Cartesian product space of those variable domains. However, the computational complexity for this calculation may grow exponentially with the number of variables L to be found at once. According to act 406, this may be an alternate consideration on the efficiency of the unknown variables because L should not be too large to make the calculation impractical. For example, Equation 4 allows the user to test multiple unknown variables at the same time, such as the effect of test results for both an MRI and an ultrasound.

Finally, according to act 408, the cost and benefit of a variable may be explicitly considered. The cost function in Equation 1 is based purely on mutual information, but can be extended to account for pre-determined (e.g., clinically biased or other customized) costs or benefits. For example, the benefit of properly diagnosing a cancer in early stages may be much larger than that of properly diagnosing that no cancer is present. In addition, even for the same disease and diagnosis conditions, health care centers may have a particular cost/benefit structure for diagnosis, which differs from other health care centers. In order to account for these additional costs and/or benefits, Equation 1 can be extended by including an additional term B:

$$\operatorname*{arg\,max}_{j \neq 0} I(X; Y_j | Z) + \gamma B(X; Y_j | Z = z) \qquad \text{(Eq. 5)}$$

B is a representation of the potential benefit gained by any given variable, and $\gamma$ is a constant controlling the relative importance of the new term. Z is shorthand to denote all the variables that have been observed. Since B could potentially specify benefits for each variable, it is defined as the expected benefit given the observed variables as:

$$B(X; Y_j | Z = z) = \sum_{x} \sum_{y_j} P(x, y_j|z) Ben(x, y_j|z) \qquad \text{(Eq. 6)}$$

Ben( ) specifies the benefit and may be defined by a clinician or a health care professional. Alternatively, the benefit Ben( ) may be determined by the health care facility which may have established benefits for different variables.

The more importance that is assigned to $\gamma$ in Equation 5, then the more likely it is that the benefit term is the sole expression that is maximized. However, if the importance, $\gamma=0$, then the expression is purely based on the existing variables or information. The additional benefit and importance considerations in Equations 4 and 5 allow for a finer control over the criteria to be optimized and therefore may give more accurate results. The importance factor $\gamma$ may be used to assign the value of a particular diagnosis over another. For example, properly diagnosing a cancer in early stages may be much more significant than properly diagnosing that no cancer is present. The importance factor ensures that a diagnosis of cancer given extra consideration by weighting the benefit term in Equation 5.

The cost/benefit considerations may assist the clinician in making the proper decision for a patient according to act 410. For example, the appropriate variable or test may be an MRI exam, whereas the second most appropriate test is ultrasound. Considering that an MRI may cost thousands of dollars and the ultrasound only costs hundreds, the clinician and the patient may prefer ultrasound over MRI. In such a circumstance, the benefit value assigned to MRI is much lower than the value assigned to ultrasound. As a result, the suggested test that the system may provide may be an ultrasound exam even though the MRI may provide additional data or additional certainty in diagnosis.

In an alternative embodiment, the system and methods described above for information maximization may be utilized in the problem of finding patients that are maximally informative about a clinical question that needs to be answered, given fixed test results. Instead of optimizing with respect to the variables to be tested, the optimization would be with respect to the value of the variables of patients to be included in the recorded clinical data.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The above disclosed subject matter is to be considered illustrative, and not restrictive or limiting, and the appended claims are intended to cover all such modifications, enhancements, and other embodiments, which fall within the true spirit and scope of the present invention. Thus, to the maximum extent allowed by law, the spirit and scope of the present invention is to be determined by the broadest permissible interpretation of the following claims, including all equivalents, and shall not be restricted or limited by the foregoing detailed description.

To clarify the use in the pending claims and to hereby provide notice to the public, the phrases "at least one of <A>, <B>, . . . and <N>" or "at least one of <A>, <B>, . . . <N>, or combinations thereof" are defined by the Applicant in the broadest sense, superseding any other implied definitions hereinbefore or hereinafter unless expressly asserted by the Applicant to the contrary, to mean one or more elements selected from the group comprising A, B, . . . and N, that is to say, any combination of one or more of the elements A, B, . . . or N including any one element alone or in combination with one or more of the other elements which may also include, in combination, additional elements not listed.

The invention claimed is:

1. In a non-transitory computer readable storage medium having stored therein data representing instructions executable by a programmed processor for proposing one of a plurality of medical tests, the storage medium comprising instructions for:
   receiving a selection of a medical condition to be treated;
   obtaining patient medical data for a particular patient that is stored in a memory;
   obtaining other medical data from existing clinical records that is stored in the memory;
   identifying at least one of the medical tests for analysis;
   analyzing the patient medical data and the other medical data with the programmed processor in communication with the memory, wherein the analysis comprises comparing each of the identified medical tests with the other medical data in view of the patient medical data for the selected medical condition;
   determining a probability for each of the identified medical tests based on the analysis of the patient medical data and the other medical data for the selected medical condition, wherein the probability comprises a likelihood of success for each of the medical tests for the particular patient for the selected medical condition, wherein the other medical data comprises results of at least some of the medical tests from the existing clinical records and those results reflect whether the medical tests were successful for other patients for the selected medical condition;
   outputting the one of the medical tests with a highest determined probability;
   utilizing the outputted medical test to obtain additional medical data, wherein the additional medical data comprises results of the medical test; and
   automatically updating the patient medical data in the memory with the additional medical data, wherein the step of analyzing the patient medical data comprises comparing each of the identified medical tests with the other medical data in view of the updated patient medical data that includes the additional medical data.

2. The computer readable storage medium of claim 1 wherein the step of analyzing further comprises:
   determining a benefit for each of the identified medical tests based on whether the medical tests were successful for other patients as reflected in the other medical data, wherein the benefit further depends on a similarity between the other medical data and the patient medical data;
   determining a cost of each of the identified medical tests; and
   maximizing a cost function with the benefit, the cost, the patient data and the other medical data.

3. The computer readable storage medium of claim 1 wherein the similarity between the other medical data and the patient medical data corresponds with a similarity between the particular patient and the other patients from the other medical data.

4. The computer readable storage medium of claim 1 wherein the medical test further comprises a potential diagnosis of a medical condition.

5. The computer readable storage medium of claim 4 wherein the diagnosis of the medical condition is added to the patient medical data.

6. The computer readable storage medium of claim 1 wherein the at least one medical test comprises a potential method of treatment to be performed, and the results of the existing clinical medical data comprises an outcome from the potential method of treatment.

7. The computer readable storage medium of claim 6 wherein the additional medical data comprises at least one result from the method of treatment.

8. The computer readable storage medium of claim 7 wherein the probability associated with the at least one medical test is adjusted by the at least one result from the method of treatment or the test, wherein the at least one result may improve the probability associated with the at least one medical test.

9. The computer readable storage medium of claim 1 wherein the determining a probability for each of the identified medical tests further comprises determining an uncertainty that reflects a similarity between the patient medical data and data from the other patients in the existing clinical records, wherein the uncertainty decreases when the data from the other patients is similar to the patient medical data.

10. The computer readable storage medium of claim 1 wherein the patient medical data comprises at least one of patient information, demographics, medical history, observations, symptoms, test results, and any combination thereof.

11. The computer readable storage medium of claim 10 wherein the at least one medical test provides at least one of the observations.

12. The computer readable storage medium of claim 1 wherein the other medical data from existing clinical records is based on a compilation of medical records of other patients.

13. The computer readable storage medium of claim 1 wherein the step of analyzing the patient medical data and the other medical data comprises:

comparing the other medical data with the patient medical data; and determining which of the at least one medical test was most effective from the other medical data or is most effective for the patient.

14. The computer readable storage medium of claim 1 wherein the step of analyzing the patient medical data and the other medical data comprises utilizing information maximization by maximizing the probability for the outputted medical test.

15. The method of claim 1 wherein the step of analyzing the patient medical data and the other medical data comprises maximizing a benefit for a patient, wherein the benefit is predetermined.

16. The computer readable storage medium of claim 1 wherein the at least one medical test comprises a combination of tests, wherein the combination of test comprises a series of tests.

17. The computer readable storage medium of claim 1 wherein the at least one medical test comprises a treatment and the step of utilizing the outputted medical test to obtain additional medical data comprising implementing the treatment, wherein the patient data is automatically updated with results from the implemented treatment.

18. The computer readable storage medium of claim 2 wherein the benefit increases a probability of the at least one medical test.

* * * * *